(12) United States Patent
Olalde Rangel

(10) Patent No.: US 7,625,587 B2
(45) Date of Patent: Dec. 1, 2009

(54) HEPATO PHYTO-NUTRACEUTICAL SYNERGISTIC COMPOSITION

(75) Inventor: Jose Angel Olalde Rangel, 519 Cleveland St., Suite 101, Clearwater, FL (US) 33755

(73) Assignee: Jose Angel Olalde Rangel, Clearwater, FL (US)

( * ) Notice: Subject to any disclaimer, the term of this patent is extended or adjusted under 35 U.S.C. 154(b) by 0 days.

(21) Appl. No.: 11/420,533

(22) Filed: Nov. 16, 2006

(65) Prior Publication Data

US 2008/0160042 A1    Jul. 3, 2008

(51) Int. Cl.
*A61K 36/00* (2006.01)
*A61K 36/258* (2006.01)

(52) U.S. Cl. .................. 424/725; 424/728
(58) Field of Classification Search .......... None
See application file for complete search history.

(56) References Cited

U.S. PATENT DOCUMENTS 5,744,187 A * 4/1998 Gaynor .............. 426/599

6,551,627 B1 * 4/2003 Yoon et al. .............. 424/725

OTHER PUBLICATIONS

HIV/AIDS Monitoring; Improved Viral Load Test Approved by FDA; Blood Weekly; Atlanta; Sep. 2002 pp. 1-2.*
Animal Models (HBV0; Trimera Disease Model Developed for Hepatitis B; Cancerweekly Plus; Atlanta; Feb. 1999 pp. 1-2.*
Davis, G. Treatment of Chronic Hepatitis C; British Medical Journal; Nov. 2001 pp. 1-3.*
Mylonakis et al. Plasma Viral Load Testing in the Management of HIV Infection; American Family Physician; Feb. 2001 pp. 1-7.*
Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*

* cited by examiner

*Primary Examiner*—Patricia Leith

(57) ABSTRACT

Phytoceutical composition for the prevention and treatment of hepatic disorders. A specific combination of extracts of plants is taught, as well as the principles for the formulations based on categorizing plants into one of three groups, Energy, Bio-Intelligence and Organization. Such combination has synergistic effects, with minimal side effects.

1 Claim, No Drawings

HEPATO PHYTO-NUTRACEUTICAL SYNERGISTIC COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat hepatic diseases. The formulation is a particular combination of plants and has a synergistic effect in combination. Principles for selecting beneficial formulation are provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process. As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines.

This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). *Conclusion*: On one hand, synthetics may have the required efficacy in th treatment of diseases; however this can be marred by severe side effects. On the other side, despite the excellent medicinal qualities of many plants, they are individually insufficient to take chronic degenerative diseases into remission. Finally, there is mounting evidence which demonstrates that medical plants contain synergistic and/or side-effect neutralizing combinations (Gilani and Rahman, 2005). Thus, what are needed in the art are better treatment regimes with improved patient tolerance, while providing sufficient efficacy.

SUMMARY OF THE INVENTION

A number of known beneficial plants were classified according to their capacity to enhance the three main elements that support overall health, in chronic degenerative diseases: Energy (E), Bio-intelligence (I) and Organization (O). A synergistic effect is expected when all three categories of herbs (E, I, O) are included in a formulation.

Thus, on the case of liver diseases, one embodiment of the invention provides an effective, natural composition for treating hepatic diseases. The composition can be used alone, or can be combined with simultaneous use of one or more pharmaceutical compositions. It can be used for the treatment of cirrhosis, cholecystitis, acute and chronic viral hepatitis, chronic alcoholic hepatopathy, fat degeneration, steato hepatitis and other liver related diseases.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients, and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only, and should not serve to unduly limit the invention.

EXAMPLE 1

Plant Characteristics—Hepatic Disorders

Energy Enhancing Components.—

*Eleutherococcus* or *Acanthopanax senticosus* (Russian Ginseng, Siberian Ginseng, Eleuthero, Devil's Shrub, Buisson du Diable, Touch-me-not, Wild Pepper, Shigoka, *Acantopanacis senticosus*, chi wu cha, ciwujia, eleutherococ, eleutherocoque, eleutherokok koljucij, ezoukogi, gashi ohgap, hongmao-wujiapi, pai wu cha pi, shigoka, Stachelkraftwurz, Stachelpanax, Taigawurzel, tsu wu cha, wu cha sang, wu cha seng, wu jia pi) contains terpenoids (oleanolic acid), glycosides (Eleutheroside A or daucosterin, B, B4, D, E, I, K, L, M), phytosterols (β-sitosterol), coumarins (Eleutheroside B1 and B3, isofraxidine), polysaccharides (eleutherans), volatile oils, caffeic acid, coniferyl aldehyde, and sugars. Eleuthero has been shown to bind to gluco or mineral corticoid receptors, and stimulate *T-lymphocyte* and natural killer cell production (immune-stimulant activity). It has anti-platelet aggregation activity similar to aspirin (which may improve micro-vascular circulation); and anti-oxidative properties. Hepatoprotector: Its lignans content (Eleutherosides B, D and E) improve hepatic function, contributing to metabolize toxic substances and medicines such as barbiturates and chemotherapeutic agents. In a smaller than 500 mg/Kg dosage, the *Eleuthero aqueous* extract demonstrates a hepatoprotective action when paracetamol and carbon tetrachloride are administered. Russian Ginseng contains at least 40 active ingredients.

*Panax ginseng* (*Chinese ginseng*, Panax, ren shen, jintsam, ninjin, *Asiatic ginseng, Japanese ginseng, Oriental ginseng, Korean red ginseng*) The main active components are ginsenosides (protopanaxadiols and protopanaxatriols types) these have been shown to have a variety of beneficial effects, including anti-inflammatory, antioxidant, and anticancer effects. 1) Energizing effect: Ginseng's active principles bind to the cellular membrane's beta-adrenergic receptors which unleashes the second messenger transduction routes (cyclic AMP). Subsequently the signal is transduced to the mitochondria to increase malate-dehydrogenase, succinate dehydrogenase and citrate synthetase activity. This increases ATP generation thus increasing the patient's energy levels. 2) Hepatoprotector-and Hepatogenerator effects: ginsenosides are capable of inhibiting metabolic reactions mediated by the microsomal CYP1A, CYP2C9 and CYP3A4 hepatic systems thus diminishing the hepatotoxicity effects of medicines and toxins. It also diminishes hepatic damage and contributes to the liver's regeneration, inhibiting or diminishing transaminase rise caused by toxins. Ginsenosides offer hepatoprotective results against ischemic reperfusion damage in the early stages of hepatic transplants. Ginsenosides also significantly increase hepatic glutathione peroxidase, reduced glutathione and dismutase superoxide at the hepatic level. 3) Anti-inflammatory effect: the phytosterols inhibit prostaglandin synthesis. 4) Other effects: Studies indicate that *Panax* enhances psychological and immune functions (unspecific cellular and humoral). Studies indicate that *Panax* improves phagocytosis, natural killer cell activity, and the production of interferon; improves physical and mental performance in mice and rats; causes vasodilatation; increases resistance to exogenous stress factors; and affects hypoglycemic activity. The incorporation of this phytomedicine provides at least 86 active principles in a single therapeutic.

*Pfaffia paniculata* (Suma, Brazilian Ginseng, Pfaffia, Para Toda, Corango-acu; also *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), six different pfaffic acids, phytosterols (sitosterol and stigmasterol) and triterpenic glycosides. It also contains saponins. Its germanium content probably accounts for its oxygenation properties at the cellular level, and its high iron content may account for its traditional use for anemia. This herb increases energy through an increase in ATP synthesis and oxygenation at the cellular level. The incorporation of this phytomedicine provides 44 active principles in a single therapeutic.

*Rhodiola rosea* (Golden Root, Roseroot) consists mainly of phenylpropanoids (rosavin, rosin, rosarin (specific to *R. rosea*), phenylethanol derivatives (salidroside, rhodioloside, tyrosol), flavanoids (catechins, proanthocyanidines, rodiolin, rodionin, rodiosin, acetylrodalgin, tricin), monoterpenes (rosiridol, rosaridin), triterpenes (daucosterol, beta-sitosterol), and phenolic acids (chlorogenic and hydroxycinnamic, gallic acids). It also contains organic acids (gallic, caffeic, and chlorogenic acids) and p-Tyrosol. There are many species of Rhodiola, but it appears that the rosavins are unique to *R. Rosea*, and it is the preferred species. It is an energizer because it activates the synthesis or resynthesis of ATP in mitochondria and stimulates reparative energy processes after intense exercise. The incorporation of this phytomedicine provides at least 20 active principles in a single therapeutic.

*Schizandra chinensis* (*Schisandra spenenthera, Schisandra berry, Chinese magnolia vine fruit*, also known as Wuweizi and Wurenchum) The major active principles of Schizandra are lignans called Schizandrins. These substances have energizing properties because they increase the activity of some enzymes which participate in the oxidative phosphorylation process. Schizandra reduces fatigue and increase exercise resistance, it also has known hepato-protective and hepato-regenerative properties. Schizandra maintains the integrity of hepatocyte cellular membranes; increases hepatic levels of ascorbic acid; inhibits NADPH oxidation; inhibits lipid peroxidation at the hepatic microsomal level as well as formation of hepatic malondialdehyde; diminishes production of carbon monoxide at the hepatic level; has an inductor effect in the enzymatic anti-toxic microsomal hepatic cytochrome P-450; increases biliary flow and the excretion of toxic substances; promotes recovery of hepatic functions; induces mRNA formation for the Hepatocyte Growth Factor (HGF); encourages the proliferation of the hepatocyte's endoplasmic smooth reticula, and accelerates the proliferation of hepatocytes; increases ornithine decarboxylase activity as well as the mitotic index, facilitates DNA synthesis and hepatic proteins; increases levels of glutathione, glutathione reductase and glucose-6-phosphate, improving the regeneration capacity of the liver. The incorporation of this phytomedicine provides at least 81 active principles in a single therapeutic.

Bio-Intelligence Modulators.—

*Andrographis paniculata* (King of Bitters, Chirettta, Kalmegh and Kiryat) Primary active principles associated with Andrographis are: flavonoids, glucosides and diterpenic lactones (andrographolides). As evidenced in various clinical studies, these substances offer immune-modulator and anti-inflammatory properties; offer hepatoprotective properties and act as hepatic antioxidatives; additionally having a choleretic effect. Studies also suggest that they stimulate the immune systems and activate macrophages. The incorporation of this phytomedicine provides at least 11 active principles in a single therapeutic.

*Astragalus membranaceus* (Huang-Qi) This plant contains three main types of active principles. Isoflavones, which act as anti-oxidants; astragalans which act as immune-stimulants and anti-inflammatory by stimulating the phagocytic activity of macrophages, of the cytotoxic response of T and NK lymphocytes and of the production and activity of interferon; and astragalans which act as modulators of the hypothalamus-hypofisis-adrenal axis response. It also conveys antioxidative properties. Hepatoprotective properties: The root extract of Astragalus protects the liver gainst damage produced by carbon tetrachloride (CC14), anticipates the drop in hepatic clucogen, and increpes the level of seric proteins and albumina. Studies have been carried out with Astragalu's extract. In one and two months the disease symptoms, the patients' quality of life and apetite improve and the levels of GPT return to normal levels. Patients with chronic hepatitis, treated with Astragalus, improve cellular immunity as welll as the phagocytosis of reticule-endothelial cells. The incorporation of this phytomedicine provides at least 38 active principles in a single therapeutic.

*Ganoderma lucidum* (Reishi, also *G. tsugae, G. valesiacum, G. oregonense, G. resinaceum, G. pfezfferi, G. oerstedli, and G. ahmadii*) is an edible fungus containing bitter triterpenoids (ganoderic acid), β-D-glucans, coumarins, alkaloids and ergosterols. These active principles confer hepatoprotective and hepato-regenerative properties because it possesses significant antiperoxidative, anti-inflammatory and antimutagenic activity due to a reduction in mediators of the immune response such as NO production and its capacity to scavenge free radicals which induce hepatic damage. Protects hepatic tissue from damage induced by toxins or drugs, inducing glutatión S-transferase activity and inhibiting beta-glucuronidasa. It offers anti-fibrosis effects in biliary cirrhosis. The polysaccharides in Ganoderma reduce the aspartate aminotransferase levels (AST), alanine aminotransferase (ALT), alkaline phosphatase, total bilirubin and LDH. It also diminishes hepatic collagen content and improves the histopathology in biliary cirrhosis, that is, it offers antifibrotic effects. It contains at least 32 active principles.

*Grifola frondosa* (Maitake, Dancing Mushroom; also *G. sordulenta, Polyporus umbellatus and Meripilus giganteus*) contains the primary polysaccharide, β-D-glucan in the 1.3 and 1.6 forms. It also contains alpha glucan, lipids, phospholipids, and ergosterol. Animal studies suggest Beta-D-glucan is an effective immune-stimulator. This substance increases the activity of macrophages and other immuno-competent cells. The substance also improves the immunological efficiency of these cells by increasing production of cytokines IL-1, IL-2 and others. The final result is an increase of defenses against infectious diseases. Various studies suggest Maitake can also be effective in the prevention and treatment of hepatic diseases. At the beginning of the 90's Chinese researchers carried out a pilot test on 32 patients with chronic hepatitis B. In an international symposium in 1994 in China the researchers showed that the results in which the patients who received Maitake had positive improvement signs (reduction in transaminase levels) when compared to the control group. In another study, a group of rats were fed a high cholesterol diet. The results were measured against complementing this diet with 20% Maitake powder. Researchers showed that Maitake inhibited the accumulation of hepatic fat. In another study, researchers fed Maitake to mice-which had autoimmune hepatic chronic damage—showing a significant imrovement. The incorporation of this phytomedicine provides at least 6 active ingredients for therapeutic use.

*Hydrastis canadensis* (golden seal, sello dorado, yellow root) contains mainly isoquinoline alkaloids (xanthopuccine, berberine, hidrastine, hidrastanine, beta-hydrastine, canadine and canadaline). These confer anti-inflammatory: Berberine inhibits activating protein 1 (AP-1), a key factor in transcription the inflammation. It also exerts a significant inhibitory effect on lymphocyte transformation, so its anti-inflammatory action seems to be due to the inhibition of DNA synthesis in the activated lymphocytes or to the inhibition of the liberation of arachidonic acid from the phospholipids of the cellular membrane. It also has immune-modulating properties by increasing the production of immunoglobulins G and M and stimulating the phagocytotic capacity of macrophages. The active principles of Hydrastis inhibit cytochrome P450 as well as microsomal hepatic fractions CYP2C9, CYP2D6 and CYP3A4, thus hindering the action of hepatoxic substances. Also, because of its antioxidative action it diminishes oxidative hepatic damage. This plant provides at least 34 active principles for therapeutic use.

*Morinda citrifolia* (Noni, Indian Mulberry, Ba Ji Tian, Nono, Nonu, Fruta de Queso and Nhau) A large range of its components have been identified. Noni encompasses at least 23 active principles, 5 vitamins and 3 minerals. Among them: several acids, vitamins (A & C), potassium, Nordamnacanthal and Morindone, anthraquinones, fitosterols, flavonolglicosides, aucubine, alizarine and others. In the range of therapeutic activities are included: 1) Immune-stimulant: The fruit's extracts inhibits tumor necrosis factor-alpha. Noni may also stimulate the release of various interleukins, including TNF-alfa, interleukine-lbeta, IL-10, IL-12, interferon-gamma and nitric oxide (NO). 2) Antioxidative function: a) In an acute hepatic-carbon tetrachloride induced-damage model, the administration of Noni, in mice, during 12 days was able to diminish lipid peroxidation and free radicals levels by 50% and 20% respectively when compared to placebo group. Another study Conclusion, Noni can protect the liver from the harmful effects of carbon tetrachloride; (b) Another study compared Noni with three known anti-oxidants: Vitamin C, grape seed powder and picnogenol, offering greater capacity to scavenge free radicals (2.8, 1.1, and 1.4 respectively). 3) Anti-inflammatory effect: The anti-inflammatory activity of Noni was measured in a carbon tetrachloride induced hepatic damage. A decrease in the inflammation foci and infiltrated lymphocytes—around central veins—was observed 6 hours after pre-treatment with Noni during 12 days prior to being exposed to carbon tetrachloride. This plant provides at least 31 active principles in a single therapeutic.

*Sutherlandia frutescens* (Cancer Bush, also *Sutherlandia microphylla*) contains *L-canavanine*, pinitol, GABA (gamma amino butyric acid), and asparagine. In addition, a novel triterpenoid glucoside known as "SU1" has been isolated and characterized. The therapeutic indications include anti-inflammatory, antioxidant, immune-modulator and vasodilator. In a recent study results suggest that an aqueous extract of S. Frutescens possesses analgesic and anti-inflammatory properties, providing sustain to its folkloric uses in the management and/or control of pain and inflammation. This Phytomedicine provide at least 5 active principles.

Organizational Improvers.—

*Angelica sinensis* (Dong Quai or Angelica, also Angelica Archangelia, Angelica Pubescens and Angelica Sylvestris) contains terpenes (terpenes, mainly β-phellandrene, with β-bisabolene, β-caryophyllene, β-phellandrene, α-and β-pinene, limonene, linalool, borneol, acetaldehyde, menthadienes and nitromenthadienes), macrocyclic lactones (including tridecanolide, 12-methyl tridecanolide, pentadecanolide), phthalates (such as hexamethylphthalate), coumarins (especially furocoumarin glycosides such as marmesin and apterin), angelicin and byakangelicin derivatives (osthol, umbelliferone, psoralen, bergapten, imperatoren, xanthotoxol, xanthotoxin, oxypeucedanin and more), as well as various sugars, plant acids, flavonoids and sterols. Contains alkyl phthalides (Ligustilide); phenylpropanoids (ferulic acid) and benzenoids. These substances stimulate the immune system's actions, through diverse lymphokines and have an anti-inflammatory effect by inhibiting 5-lipoxygenase and elastase, as well as selectively inhibiting 12-(S)-HHTrE production, a marker of cyclo-oxygenase activity. Angelica also exhibits antihepatoxicity activity: the intraperitoneal administration of a root decoction improved the galactosamine induced hepatotoxicity in rats. Ferulic acid, one of the plant's root components protected the hepatic mitochondria from free oxygen radical induced hepatic damage. A pre-treatment with sodium ferulate during ten days improved the hepatic toxicity induced by paracetamol, prednisolone and bromobenzene in mice. The incorporation of this phytomedicine into compositions provides at least 70 active principles in a single therapeutic.

*Bupleurum chinense* (*Bupleurum falcatum*, Thorowax, Saiko, *Hare's ear*, Chai Hu) The active principles are triterpene saponins (saikosaponins A, B1 a B4, D, E, F, H); saikogenines A-G and polysaccharides (bupleurans 2IIb y 2IIc). These substances grant anti-inflammatory properties of similar potency as prednisolone as well as immune regulatory activity, because it activates macrophages, stimulating the growth response of lymphocytes T and increasing the production of interleukine-2. This plant offers hepatoprotective and hepatoregenerating capabilities, regulating hepatic functions and inhibiting transaminase levels caused by damage to the hepatic tissue. The incorporation of this phytomedicine into compositions provides at least 26 active principles in a single therapeutic.

*Coptis chinensis* (*C. deltoidea, C. teetoides, C. omeiensis, Coptis, Coptis root*, ChuanLian, Ya Lian, Ji Shua Lian, Huang lian and Wei Lian) and its dried rhizome *Rhizoma coptidis* contain berberine and protoberberine alkaloids (3, 8, and 10). Berberine inhibits activating protein 1 (AP-1), a key factor in transcription the inflammation. It also exerts a significant inhibitory effect on lymphocyte transformation, so its anti-inflammatory action seems to be due to the inhibition of DNA synthesis in the activated lymphocytes or to the inhibition of the liberation of arachidonic acid from the phospholipids of the cellular membrane. It also has immune-modulating properties by increasing the production of immunoglobulins G and M and stimulating the phagocytotic capacity of macrophages. The incorporation of this phytomedicine into compositions provides at least 18 active principles in a single therapeutic.

*Glycyrrhizae radix* (Gan Cao, *Uralensis radix*) Its main active principles are: Saponosides (5-13%): glicirricine, 24-OH-glicirricine, glabranines A y B, glicirretol, glabrólido, isoglabrólido. Flavonoids: flavanones (liquiritigenin, liquiritin), chalcones, isoflavonoids (neoliquiritin, hispaglabridin). Triterpene sterols. Polysaccharides (GA), starch (25-30%), glucose and saccharose (3-10%). The roots of this plant correspond to the dried up roots of Glycyrrhiza glabra. It contains at least 4% of glicirricinic acid. The normalized ethanolic fluid extract of licorice contains between 3% and 5% of glicirricinic acid. This acid reduces the toxic action of carbon tetrachloride and of galactosamine in mice hepatocytes trough its antioxidant activity. Glycyrrhizin inhibited the liberation of histamine in mice hepatocytes and prevented hepatic injuries induced by carbon tetrachloride and citotoxicity mediated by macrophages. The intragastric administration to mice of flavonoid fractions isolated from licorice protected against carbon tetrachloride hepatotoxicity. Glycyrrhizin protected the liver through membrane stabilizing effects. The anti-inflammatory and anti-allergic properties of this plant are attributed to the activity of glycyrrhzin and glycyrrhetic acid (enoxolone) which are similar to that of corticosteroids. These active principles act indirectly boosting the activity of corticosteroids. In vitro, glycyrrhetic acid inhibits beta-reductase, an enzyme that competitively inactivates steroid hormones and 11_beta-hydroxysteroid dehydrogenase, the enzyme that metabolizes cortisol. The incorporation of this phytomedicine into compositions provides at least 380 active principles in a single therapeutic.

*Picrorhiza kurroa* (Kutki, Karoo) The most important active constituents are the iridoid glycoside picrosides I, II, and III, and kutkoside, known collectively as kutkin. Though less well researched than Silybum, appears to have similar applications and mechanisms of action. When compared with Silybum, the curative efficacy of Picrorhiza was found to be similar, or in many cases superior, to the effect of Silybum. Picrorrhiza possesses significant antioxidant activity, by reducing lipid peroxidation and free radical damage. Like silymarin, it also has an effect on liver regeneration. Picrorrhiza also offers anti-inflammatory effects inhibiting the infiltration of pro-inflammatory cells as neutrophils, macrophages, and mast cells. One of its minor components, apocynin, exhibits powerful anti-inflammatory effects, without affecting beneficial activities such as phagocytosis and chemotaxis or humoral immunity. The incorporation of this phytomedicine into compositions provides at least 20 active principles in a single therapeutic.

*Smilax regelii* (*S. ornate, S. aristolochiaefolia, S. febrifiga, S. ovalifolia, S. lancaefolia*) The main active principles are fitosterols (sitosterols β and ε, stigmasterol, sitosterol-d-glucoside) and steroid saponins (sarsasapogenin, sarsaponin, smilagenin, diosgenine, tigogenin, asparagines, laxogenin) Flavonoids (quercetin and kaempferol) and minerals (Al, Cr, Co, P, Fe, Mg, Mn, K, Se, Si, Zn). Smilax improves the hepatic and renal excretory function, enhancing the removal of toxic substances and waste from cells, blood vessels and lymphatic system. The incorporation of this phytomedicine into compositions provides at least 35 active principles in a single therapeutic.

*Silybum marianum* (*Carduus marianus*, Holy thistle, Marian thistle, and Mary thistle) The main active principles are: flavonolignans, including Silibine, Silibinin, Silicristine, Isosilibinin and Silidianin, collectively known as Sylimarin. This compound has the highest grade of hepato-protective, hepato-regenerating, and anti-inflammatory activity. Mechanisms which explain its therapeutic properties are diverse and include: anti-oxidation; lipidic anti-peroxidation; improvement in detox capacity through a competitive inhibition with toxic substances; and protection against glutathione depletion. Another mechanism which explains its therapeutic properties is the increase of protein synthesis, obtained thanks to a significant reinforcement of ribosome formation, DNA and proteins synthesis, due to active principles bonding to polymerase receptors, stimulating ribosome formation. Silybum seeds contain betaine, a demonstrated hepatoprotector, and essential fatty acids which contribute to sylimarin's anti-inflammatory effects. Anti-inflammatory effects are due to mastocytes stabilization, inhibition of neutrophils, and strong inhibition of leucotrien and prostaglandin formation. Silimarin inhibits intestinal enzymes such as beta-glucuronidase, thus improving the glucuronization, important stage in hepatic detox. More body toxins are removed via glucuronization than through other detox pathways. In vitro experiments with damage induced—paracetamol, cisplatin and vincristin—cells have demonstrated that the administration of silibinin before or after the chemical damage can diminish or prevent the hepatoxic effect. Studies have demonstrated the hepatoprotective and immune-modulator effects of sylimarin, normalizing elevated levels of aspartate amino transferase, alanine amino transferase and serum bilirubin, markedly reducing the high levels of gamma-glutamyl transferase. No side effects have been reported. The incorporation of this phytomedicine into compositions provides at least 57 active principles in a single therapeutic.

EXAMPLE 2

Composition—Hepatic Disorders

A particularly preferred composition is shown in Table 1. Ratios reflect the concentration of active ingredient over the natural state, and the amounts provided are mg of extract. Obviously, the amount should be increased where the strength is reduced, and vice versa.

TABLE 1

Herbaria

| Active Agent | Ratio | Amount (mg) |
|---|---|---|
| Energy enhancers | | |
| *Eleutherococcus senticosus* root extract | 5:1 | 42.09 |
| *Panax ginseng* root extract | 5:1 | 12.63 |
| *Pfaffia paniculata* (Suma) root extract | 4:1 | 26.31 |
| *Rhodiola rosea* root extract | 5:1 | 7.58 |
| *Schizandra chinensis* | 5:1 | 12.63 |
| Bio-Intelligence modulators | | |
| *Andrographis paniculata* | 5:1 | 84.19 |
| *Astragalus membranaceus* root extract | 5:1 | 84.19 |
| *Ganoderma lucidum* mushroom extract | 6:1 | 84.19 |
| *Grifola frondosa* mushroom extract | 10:1 | 16.84 |
| *Hydrastis canadensis* root extract | 5:1 | 25.26 |
| *Morinda citrifolia* | 5:1 | 42.09 |
| *Sutherlandia frutescens* extract | 1:1 | 12.63 |
| Organization improvers | | |
| *Angelica sinensis* root extract | 5:1 | 42.09 |
| *Bupleurum falcatum* root extract | 5:1 | 21.05 |
| *Coptis chinensis* plant extract | 1:1 | 21.05 |
| *Glycyrrhizae radix* root extract | 1:1 | 12.63 |
| *Picrorhiza kurroa* rhizome extract | 4:1 | 26.31 |
| *Silybum marianum* | 5:1 | 84.19 |
| *Smilax regelii* | 5:1 | 42.09 |
| Total | | 700 mg |

EXAMPLE 3

A Clinical Study of Formulation's Effectiveness and Tolerance

A three month long retrospective, descriptive, multicenter clinical study was undertaken to evaluate the effects of the formulation—subject of this patent request—through the measurement of changes observed in transaminase—and Bilirubin—seric levels in 46 patients with chronic hepatopathy. The treatment—consisting of seven 700 mg capsules, three times a day—significantly decreased transaminase in 96.4% of all patients; and reduced bilirubin levels in 86.95% of patients. The symptoms—associated with the pathology—disappeared after one month of treatment and thus the Quality of Life improved, remaining asymptomatic during the last 2 months of the study. There were no side effects in any of the patients. The formulation—object of this patent request—avoided the severe side effects caused by synthetic drugs used in chronic liver diseases.

EXAMPLE 4

Principles for Selecting Synergistic Combinations

In order to explain the formulation encompassed by the invention, we have categorized beneficial plants into one of three groups, each of which should be present for synergistic effect. The classifications are Energy, Bio-Intelligence and Organization. Plants classified under Energy are associated with ATP synthesis (such as the Krebs cycle, oxidative phosphorylation, beta-oxidation, etc.). Plants classified under Bio-Intelligence are those that regulate the neuroendocrine and immunological systems and cellular processes, thus controlling the interactions between the various systems in the body. Finally, plants classified under Organization are those that relate to the structure and function of specific organs. Combinations of plants from these three classification groups have synergistic effect because they address each necessary component for total health—in effect they provide the triangle on which healing is fully supported.

An illustrative example of synergy in medicinal plants is an in vitro study that demonstrates how the activity of herbal Berberine alkaloids is strongly potentiated by the action of 5'-methoxyhydnocarpin (5'MHC)—an active principle of another phytomedicine (denominated Hydnocarpus wightiana). It shows a strong increase of accumulation of berberine in the cells in the presence of 5'—MHC, indicating that this plant compound effectively disabled the bacterial resistance mechanism against the berberine antimicrobial, thus showing the synergy of both substances. Stermitz FR, et al., Synergy in a medicinal plant: antimicrobial action of berberine potentiated by 5'-methoxyhydnocarpin, a multidrug pump inhibitor. Proc Nat'l Acad Sci USA. Feb. 15, 2000; 97(4):1433-7.

We expect to further demonstrate synergistic effect on a molecular scale by studying the gene expression profile changes in response to various plant ingredients and combinations thereof. Experiments are already underway demonstrating the expression profile in response to these formulations. We will be aided in this work because researchers have already begun studying the expression profiles of various medicinal plants, thus providing a database of knowledge from which to build. E.g. Hsu YL, Kuo PL, Chiang LC, Lin CC. Involvement of p53, nuclear factor kappaB and Fas/Fas ligand in induction of apoptosis and cell cycle arrest by saikosaponin d in human hepatoma cell lines. Cancer Lett. Sep. 30, 2004;213(2):213-21.

We may also test combinations of plants for further demonstration of synergistic effects by using experimental models.

The invention claimed is:

1. A phyto-nutraceutical composition, comprising *Eleutherococcus senticosus* root extract, 42.09 mg; *Panax ginseng* root extract, 12.63 mg; *Pfaffia paniculata* (Suma) root extract, 26.31 mg; *Rhodiola rosea* root extract, 7.58 mg; *Schizandra chinensis*, 12.63 mg; *Andrographis paniculata*, 84.19 mg; *Astragalus membranaceus* root extract, 84.19 mg; *Ganoderma lucidum* mushroom extract, 84.19 mg; *Grifola frondosa* mushroom extract, 16.84 mg; *Hydrastis canadensis* root extract, 25.26 mg; *Morinda citrifolia,* 42.09 mg; *Sutherlandia frutescens* extract, 12.63 mg; *Angelica sinensis* root extract, 42.09 mg; *Bupleurum falcatum* root extract, 21.05 mg; *Coptis chinensis* plant extract, 21.05 mg; *Glycyrrhizae radix* root extract, 12.63 mg; *Picrorhiza kurroa* rhizome extract, 26.31 mg; *Silybum marianum*, 84.19 mg; *Smilax regelii,* 42.09 mg; and optionally including water or gelatin.

* * * * *